US008357800B2

(12) United States Patent
Nazeeruddin et al.

(10) Patent No.: US 8,357,800 B2
(45) Date of Patent: Jan. 22, 2013

(54) BIPYRIDINE METAL COMPLEXES FOR USE AS LIGHT-EMITTING MATERIAL

(75) Inventors: Mohammad Khaja Nazeeruddin, Ecublens (CH); Etienne David Baranoff, Renens Vd (CH); Michael Graetzel, Saint Sulpice (CH)

(73) Assignee: SOLVAY (Societe Anonyme), Brussels (BE)

( * ) Notice: Subject to any disclaimer, the term of this patent is extended or adjusted under 35 U.S.C. 154(b) by 419 days.

(21) Appl. No.: 12/602,815

(22) PCT Filed: Jun. 5, 2008

(86) PCT No.: PCT/EP2008/056954
§ 371 (c)(1),
(2), (4) Date: Dec. 3, 2009

(87) PCT Pub. No.: WO2008/148830
PCT Pub. Date: Dec. 11, 2008

(65) Prior Publication Data
US 2010/0174078 A1    Jul. 8, 2010

(30) Foreign Application Priority Data

Jun. 8, 2007   (EP) .................................... 07109876

(51) Int. Cl.
*C07F 15/00* (2006.01)
(52) U.S. Cl. ........................................................... 546/4
(58) Field of Classification Search ..................... 546/4
See application file for complete search history.

(56) References Cited

U.S. PATENT DOCUMENTS

| | | | |
|---|---|---|---|
| 6,670,645 B2 | 12/2003 | Grushin et al. | |
| 7,482,450 B2 | 1/2009 | Bach et al. | |
| 2005/0214576 A1 | 9/2005 | Lamansky et al. | |
| 2006/0008670 A1 | 1/2006 | Lin et al. | |
| 2006/0024522 A1 | 2/2006 | Thompson | |
| 2009/0115327 A1 | 5/2009 | Nazeeruddin et al. | |
| 2009/0200920 A1 | 8/2009 | Jin et al. | |

FOREIGN PATENT DOCUMENTS

| | | |
|---|---|---|
| JP | 20030113163 A | 4/2003 |
| JP | 20030113164 A | 4/2003 |
| WO | WO 2004085449 A1 | 10/2004 |
| WO | WO 2005117159 A1 | 12/2005 |
| WO | WO 2005117160 A1 | 12/2005 |
| WO | WO 2007042474 A2 | 4/2007 |
| WO | WO 2007115972 A1 | 10/2007 |
| WO | WO 2008043815 A1 | 4/2008 |
| WO | WO 2008148829 A1 | 12/2008 |

OTHER PUBLICATIONS

Neve et al. "Synthesis, Structure, Photophysical Properties, and Redox Behavior of Cyclometalated Complexes of Iridium(III) with Functionalized 2,2'-Bipyridines" Inorganic Chemistry, 1999, vol. 38, No. 10, pp. 2250-2258.*

Slinker et al. "Green electroluminescence from an ionic iridium complex" Applied Physics Letters, 2005, vol. 86, No. 173506, pp. 1-3.*
M.A. Baldo et al—"Very high-efficiency green organic light-emitting devices based on electrophosphorescence" —Applied Physics Letters 1999, vol. 75(1), p. 4-6
K. Dedeian et al—"A new synthetic route to the preparation of a series of strong photoreducing agents : fac tris-ortho-matalated complexes of iridium (III) with substituted 2-phenylpyridines" —Inorg. Chem. 1991, vol. 30, p. 1685-1687.
F.O. Garces et al—"Synthesis, structure, electrochemistry and photophysics of methyl-substituted phenylpyridine ortho-metalated iridium (III) complexes" —Inorg. Chem. 1988, vol. 27, p. 3464-3471.
Mirco G. Colombo et al—"Facial tris cyclometalated Rh(3+) and Ir(3+) complexes : their synthesis, structure and optical spectroscopic properties" —Inorg. Chem. 1994, vol. 33, p. 545-550.
J.H. Van Diemen et al—"Synthesis, X-ray structure, electrochemical and electronic properties of [3-(pyridin-2yl)-4-methyl-1,2,4-triazole-bis-(2-(2'-phenylato)pyridine)-iridium(III)] hexafluorophosphate" —Inorganica Chimica Acta vol. 181, (1991), p. 245-251.
Janos Rohonczy et al—"Trimethylsilylated N-alkyl-substituted carbamates III Structure of trimethylsilyl-N,N-diisopropyl carbamate in solid phase and in solution"—Journal of Organometallic Chemistry vol. 340 (1988), p. 293-302.
K.A. King et al—"Excited-state properties of a triply ortho-metalated iridium(III) complex"—J. Am. Chem. Soc. 1985, vol. 107, p. 1431-1432.
Olivier Lohse et al—"The palladium catalyzed Suzuki coupling of 2- and 4-chloropyridines"—Synlett 1999, N°1, p. 45-48.
S. Sprouse et al—"Photophysical effects of metal-carbon sigma bonds in ortho-metalated complexes of Ir(III) and Rh(III)"—J. Am. Chem. Soc. 1984, vol. 106, p. 6647-6653.
Jason D. Slinker et al—"Efficient yellow electroluminescence from a single layer of a cyclometalated iridium complex"—J. Am. Chem. Soc. 2004, vol. 126, p. 2763-2767.
Jason D. Slinker et al—"Green electroluminescence from an ionic iridium complex"—Applied Physics Letters vol. 86, p. 173506/1-173506/3 (2005).
Sergey Lamansky et al—"Synthesis and characterization of phosphorescent cyclometalated iridium complex"—Inorg. Chem. 2001, vol. 40, p. 1704-1711.
Sergey Lamansky et al—"Highly phosphorescent bis-cyclometalated iridium complexes : synthesis, photophysical characterization and use in organic light emitting diodes"—J. Am. Chem. Soc. 2001, vol. 123, p. 4304-4312.

(Continued)

*Primary Examiner* — Joseph Kosack
(74) *Attorney, Agent, or Firm* — Foley & Lardner LLP

(57) ABSTRACT

The present invention relates to light emitting materials comprising novel ortho-metalated transition metal complexes [C^N]$_2$M[N^N] comprising two orthometalated ligands (C^N ligands) and a neutral bidentate bipyridine ligand (N^N). Surprisingly, it has been found that when the metal binds both orthometalated chelate C^N ligands and a neutral bidentate bipyridine ligand (N^N), these ligands participate in the emission process, thus greatly improving the red emission efficiency of complexes [C^N]$_2$M[N^N]. The present invention further relates to the use of such light emitting materials and an organic light emitting device comprising such light emitting material.

13 Claims, 1 Drawing Sheet

OTHER PUBLICATIONS

Francesco Neve et al—"Synthesis, structure, photophysical properties and redox behavior of cyclometalated complexes of iridium(III) with functionalized 2,2'-bipyridines"—Inorg. Chem. 1999, vol. 38, p. 2250-2258.

Rachel C. Evans et al—"Coordination complexes exhibiting room-temperature phosphorescence : evaluation of their suitability as triplet emitters in organic light emitting diodes"—Coordination Chemistry Reviews vol. 250 (2006), p. 2093-2126.

Marc Lepeltier et al—"Synthesis, structure and photophysical and electrochemical properties of cyclometallated iridium(III) complexes with phenylated bipyridine ligands"—Eur J. Inorg. Chem. 2005, p. 110-117.

U.S. Appl. No. 12/444,793, filed Apr. 8, 2007, Nazeeruddin et al.

U.S. Appl. No. 12/602,811, Nazeeruddin et al.

* cited by examiner

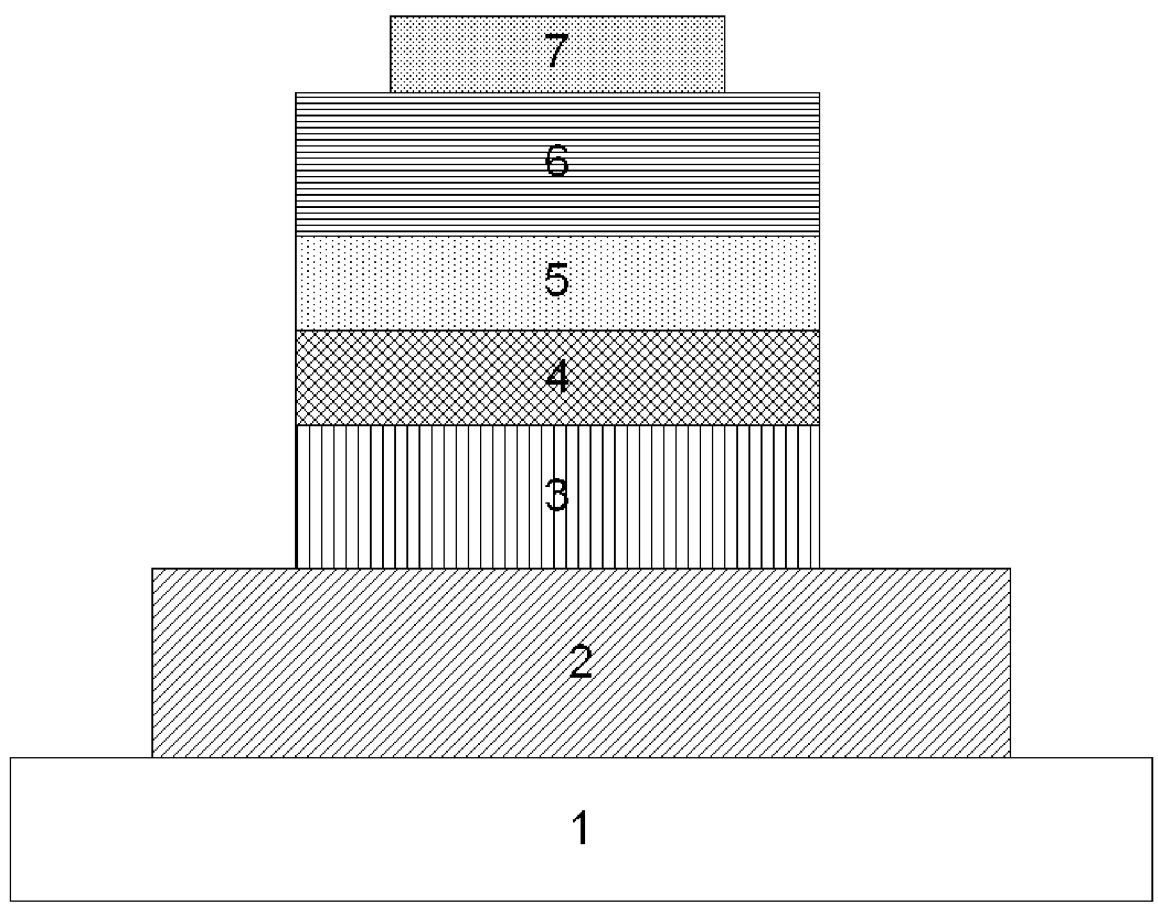

BIPYRIDINE METAL COMPLEXES FOR USE AS LIGHT-EMITTING MATERIAL

CROSS-REFERENCE TO RELATED APPLICATIONS

This application is a U.S. national stage application under 35 U.S.C. §371 of International Application No. PCT/EP2008/056954 filed Jun. 5, 2008, which claims priority to European Application No. 07109876.8 filed Jun. 8, 2007, these applications being incorporated herein by reference in their entirety for all purposes.

TECHNICAL FIELD

The present invention relates to a light-emitting material, the use of said material and a light-emitting device capable of converting electrical energy into light.

BACKGROUND ART

Today, various display devices have been under active study and development, particularly those based on electroluminescence (EL) from organic materials.

In contrast to photoluminescence (i.e., light emission from an active material due to optical absorption and relaxation by radioactive decay of excited state), electroluminescence (EL) is a non-thermal generation of light resulting from the application of an electric field to a substrate. In the latter case, excitation is accomplished by the recombination of charge carriers of contrary signs (electrons and holes) injected into an organic semiconductor in the presence of an external circuit.

A simple prototype of an organic light-emitting diode (OLED), i.e., a single layer OLED, is typically composed of a thin film of an active organic material, which is sandwiched between two electrodes, one of which needs to be semitransparent in order to observe light emission from the organic layer. Usually, an indium tin oxide (ITO)-coated glass substrate is used as an anode.

If an external voltage is applied to the two electrodes, then charge carriers (i.e., holes) at the anode and electrons at the cathode are injected to the organic layer beyond a specific threshold voltage depending on the organic material applied. In the presence of an electric field, charge carriers move through the active layer and are non-radioactively discharged when they reach the oppositely charged electrode. However, if a hole and an electron encounter one another while drifting through the organic layer, then excited singlet (anti-symmetric) and triplet (symmetric) states (i.e., so-called excitons) are formed. Light is thus generated in the organic material from the decay of molecular excited states (or excitons). For every three triplet excitons that are formed by electrical excitation in an OLED, only one symmetric state (singlet) exciton is created.

Many organic materials exhibit fluorescence (i.e., luminescence from a symmetry-allowed process) from singlet excitons. Since this process occurs between states of same symmetry, it may be very efficient. On the contrary, if the symmetry of an exciton is different from the one of the ground state, then the radioactive relaxation of the exciton is disallowed and luminescence will be slow and inefficient. Because the ground state is usually anti-symmetric, the decay from a triplet breaks symmetry. The process is thus disallowed and the efficiency of EL is very low. Therefore, the energy contained in the triplet states is mostly wasted.

Luminescence from a symmetry-disallowed process is known as phosphorescence. Characteristically, phosphorescence may persist up to several seconds after excitation due to the low probability of the transition, which is different from fluorescence that originates in the rapid decay.

However, only a few organic materials have been identified, which show efficient room temperature phosphorescence from triplets.

Successful utilization of phosphorescent materials holds enormous promises for organic electroluminescent devices. For example, one advantage of utilizing phosphorescent materials is that all excitons (formed by combining holes and electrons in an EL), which are (in part) triplet-based in phosphorescent devices, may participate in energy transfer and luminescence. This can be achieved either by phosphorescence emission itself or by using phosphorescent materials to improve the efficiency of fluorescence process.

In each case, it is important that the light emitting material provides electroluminescence emission in a relatively narrow band centered near selected spectral regions, which correspond to one of the three primary colours (i.e., red, green and blue). This is so that they may be used as a coloured layer in an OLED.

As a means for improving the properties of light-emitting devices, there has been reported a green light-emitting device utilizing the emission from ortho-metalated iridium complex. (Ir(ppy)3: tris-ortho-metalated complex of iridium (III) with 2-phenylpyridine (ppy). *Appl. phys. lett.* 1999, vol. 75, p. 4.

Thus, US 2005214576 (SERGEY LAMANSKY ET AL.) 29 Sep. 2005 discloses emissive phosphorescent organometallic compounds useful in the fabrication of organic light emitting devices, which are exemplified by the following: platinum(II)(2-phenylpyridinato-N,$C^{2'}$)(acetyl acetonate) [Pt(ppy)(acac)]; platinum(II)(2-(p-tolyppyridinato-N,$C^{2'}$) (acetyl acetonate) [Pt(tpy)(acac)]; platinum(II)(7,8-benzoquinolinato-N,$C^{3'}$) (acetyl acetonate) [Pt(bzq)(acac)]; platinum(II)(2-benzylpyrinato-N,$C^{2'}$) (acetyl acetonate) [Pt(bzpy)(ocac)]; platinum(II)(2-(2'-thienyl)pyridinato-N,$C^{3'}$) (acetyl acetonate) [Pt(thpy)(acac)]; platinum(II)(2-(2'-(4',5'-benzothienyl)pyridinato-N,$C^{3'}$) (acetyl acetonate) [Pt(btp)(acac)]; platinum(II)(2-(4',6'-difluorophenyl)pyridinato-N,$C^{2'}$) (acetyl acetonate) [Pt(4,6-$F_2$ ppy)(acac)]; platinum(II)(2-(4',5'-difluorophenyl)pyridinato-N,$C^{2'}$) (acetyl acetonate) [Pt(4,5-$F_2$ ppy)(acac)]; and platinum(II)(2-(4',5'-difluorophenyl)pyridinato-N,$C^2$) (2-picolinato) [Pt(4,5-$F_2$ ppy)(pico)].

WO 2005/117159 (CDT OXFORD LIMITED) 8 Dec. 2005 discloses a metal complex for emitting light represented by formula I, which is shown below:

M-L wherein M is a metal, L is a ligand and L comprises Ar that is a substituted or unsubstituted heteroaryl ring, which contains at least one phosphorus atom. This suggests that L is preferably a bidentate ligand such as bipyridyl.

WO 2005/117160 (CDT OXFORD LIMITED) 8 Dec. 2001 discloses a charged metal complex useful for light emitting devices. The charged metal complex may be fluorescent or phosphorescent, which contains metal M and coordinate ligand L. Suitable metals M include lanthanide metals, d-block metals and metals forming fluorescent complexes. Further, ligand L may be monodentate, bidentate or tridentate.

SPROUSE, S., et al. Photophysical effects of metal-carbon a bonds in ortho-metalated complexes of Ir(III) and Rh(III). *J. Am. Chem. Soc.* 1984, vol. 106, p. 6647-6653. disclose dichloro-bridged dimmers of the type [M(L)$_2$Cl]$_2$, wherein L is 2-phenylpyridine (ppy) or benzo[h]quinoline (bzq) and M is Rh(III) or Ir(III). The above reference teaches that the ortho-metalated ligands exhibit considerably higher spectroscopic effects and lower energy charge transfer transitions compared to Rh(III) and Ir(III) complexes of 2,2'-bipyridine (bpy) and 1,10-phenanthroline (phen).

SLINKER, Jason D., et al. Efficient yellow electroluminescence from a single layer of a cyclometalated iridium complex. *J. Am. Chem. Soc.* 2004, vol. 126, p. 2763-2767. disclose a charged iridium complex, [Ir(ppy)$_2$-(dtb-bpy)]$^+$ (PF$_6$)$^-$, and its use as a multifunctional cyclometalating ligands. The charged iridium complex contains three ligands, wherein two cyclometalating ligands (ppy: 2-phenylpyridine) are chosen to coordinate the iridium metal center to further increase the ligand field splitting energy. Further, the third ligand, 4,4'-di-tert-butyl-2,2'-dipyridyl (dtb-bpy), ensures redox reversibility, decreases self-quenching and enhances device characteristics.

LEPELTIER, Marc, et al. Synthesis, structure and photophysical and electrochemical properties of cyclometallated iridium(III) complexes with phenylated bipyridine ligands. *Eur. J. Inorg. Chem.* 2005, p. 110-117. disclose a series of cationic diiminoiridium(III) complexes, [Ir(ppy-N,C)$_2$(L-N, N)](PF$_6$)(Hppy=2-phenylpyridine, L=4,4'-$tBu_2$dpbpy, 4,4'-Me$_2$dpbpy, 4,4'-Me$_2$pbpy, 4,4'-Me$_2$bpy), and their photophysical and electrochemical properties.

SLINKER, Jason D., et al. Green electroluminescence from an ionic iridium complex. *Appl. phys. lett.* 2005, vol. 86, p. 173506. disclose green fluorescence from an ionic iridium complex, [Ir(F-mppy)2(dtb-ppy)]$^+$(PF6$^-$), wherein F-mppy is 2-(4'-fluorophenyl)-5-methylpyridine and dtb-bpy is 4,4'-di-tert-butyl-2,2'-bipyridine.

EVANS, Rachel C., et al. Coordination complexes exhibiting room-temperature phosphorescence: Evaluation of their suitability as triplet emitters in organic light emitting diodes. *Coordination Chemistry review.* 2006, vol. 150, p. 2093-2126. disclose several iridium(III) complexes containing cyclometalated ligands such as
4-(4'-chlorophenyl)-6'-phenyl-2,2'-bipyridine (clpby),
4'-(4-carboxyphenyl)-6'-phenyl-2,2'-bipyridine (cpbpy),
4,4'-dibutyl-2-2'-bipyridine (dbbpy),
4-(4-hydroxyphenyl)-6'-phenyl-2,2'-bipyridine (hpbpy) or
4'-(4-tolyl)-6'-phenyl-2,2'-bipyridine and its derivatives.

However, since the above light-emitting materials of the prior art do not display pure colours, i.e., their emission bands, which are generally limited to green, are not centered near selected spectral regions (corresponding to one of the three primary colours—red, green and blue), the range that they can be applied as OLED active compound is narrow. It has thus been desired to develop light-emitting materials, which are capable of emitting light with other colours, especially in the red region.

Efficient and long-lived red-light emitters with good colour coordinates are a recognized current shortfall in the field of organic electroluminescent devices.

DISCLOSURE OF INVENTION

It is thus an object of the present invention to provide a light emitting material comprising an ortho-metalated complex with an ancillary ligand, as described below.

Another object of the present invention is the use of said light emitting material, as well as to provide an organic light emitting device comprising said light emitting material.

As mentioned above, the object of the present invention is to provide a light emitting material, which comprises the complex of formula (I):

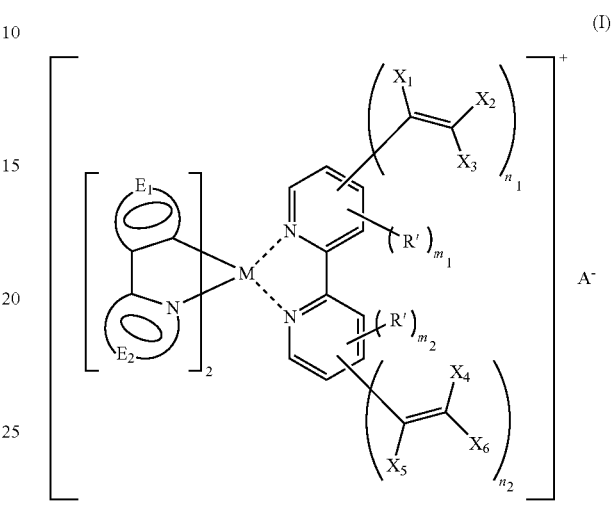

wherein:

M represents a transition metal having an atomic number of at least 40, which is preferably in groups 8 to 12, more preferably Ir or Pt, and most preferably Ir;

$E_1$ represents an aromatic or heteroaromatic ring optionally condensed with additional aromatic moieties or non aromatic cycles, wherein said ring optionally has one or more substituents and optionally forms a condensed structure with the ring comprising $E_2$, and wherein said ring coordinates to metal M by using a sp$^2$ hybridized carbon;

$E_2$ represents a N-containing aromatic ring optionally condensed with additional aromatic moieties or non aromatic cycles, wherein said ring optionally has one or more substituents and optionally forms a condensed structure with the ring comprising $E_1$, and wherein said ring coordinates to metal M by using a sp$^2$ hybridized nitrogen;

R' is the same or different at each occurrence and is selected from the group consisting of —H, —F, —Cl, —Br, —NO$_2$, —CN, a straight or branched $C_{1-20}$ alkyl, a $C_{3-20}$ cyclic alkyl, a straight or branched $C_{1-20}$ alkoxy, a $C_{1-20}$ dialkylamino, a $C_{4-14}$ aryl, a $C_{4-14}$ heteroaryl that may be substituted by one or more non aromatic radicals, wherein a plurality of substituents R' (either on the same ring or on two different rings) may collectively form an additional mono- or polycyclic ring system (optionally aromatic);

$X_1$, $X_2$, $X_3$, $X_4$, $X_5$ and $X_6$ are the same or different at each occurrence and are independently selected from hydrogen, alkyl, aryl, heteroaryl and alkyl, each of which may be substituted by at least one substituent;

A$^-$ is a counter anion; and $n_1$, $n_2$, $m_1$ and $m_2$ are the same or different at each occurrence and represent an integer from 0 to 4, wherein $n_1+m_1=4$ and $n_2+m_2=4$, provided that $n_1$ and $n_2$ cannot be zero at the same time.

As specified above in formula (I), the two chelating monoanionic ligands are bound to the metal through carbon and nitrogen atoms, and comprises $E_1$ and $E_2$ moieties. Such ligands are generally denoted as orthometalated ligands ("C^N ligands").

The chelating bidentate bipyridine ligand bound to the metal through two nitrogen atoms is generally denoted as ancillary ligand ("N^N ligand").

Surprisingly, it has been found that when the neutral chelate ligand (N^N) (also referred to as ancillary ligand) comprises a 2,2'-bipyridine bearing conjugated ethylenically unsaturated substituents to thereby possess adequate electron-accepting properties, said ligand advantageously participates in the emission process. That is, such ligand significantly shifts emission toward lower energies (red-shift) and substantially improves the emission efficiency of complexes $[C^N]_2M[N^N]$ in the red region.

Further, through the chelate ligand (NAN) bearing conjugated ethylenically unsaturated substituents, it is possible to obtain highly phosphorescent light emitting materials comprising $[C^N]_2M[N^N]$ complexes of formula (I), which has a maximum emission between 650 nm and 750 nm, thus corresponding to a red emission.

Preferably, the light emitting material of the present invention comprises the complex of formula (II):

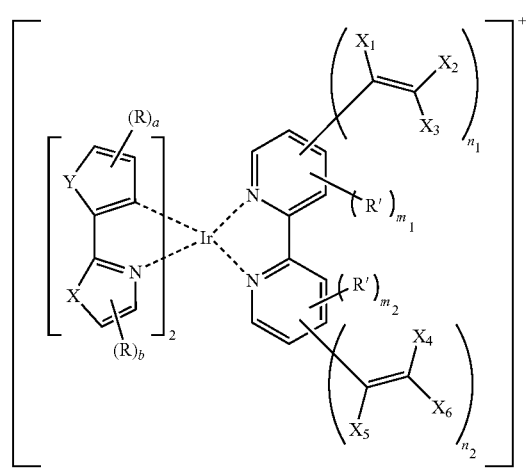

(II)

wherein:

$X_1, X_2, X_3, X_4, X_5, X_6$, R', $n_1, n_2, m_1, m_2$ and $A^-$ have the same meanings as defined above;

X is chosen from the group consisting of —CH=CH—, —CR=CH—, —CR=CR—, N—H, N—$R^1$, O, S and Se, wherein X is preferably selected from —CH=CH—, —CR=CH— or S;

Y is chosen from the group consisting of —CH=CH—, —CR=CH—, —CR=CR—, N—H, N—$R^1$, O, S and Se, wherein Y is preferably selected from CH=CH—, —CR=CH— or S;

R is the same or different at each occurrence and represents —F, —Cl, —Br, —$NO_2$, —CN, a straight or branched $C_{1-20}$ alkyl, a $C_{3-20}$ cyclic alkyl, a straight or branched $C_{1-20}$ alkoxy, a $C_{1-20}$ dialkylamino, a vinyl that may be substituted by one or more aromatic or non aromatic radicals, a $C_{4-14}$ aryl, a $C_{4-14}$ heteroaryl that may be substituted by one or more non aromatic radicals, wherein a plurality of substituents R (either on the same ring or on two different rings) may collectively form an additional mono- or polycyclic ring system (optionally aromatic);

a is an integer from 0 to 4; and b is an integer from 0 to 4.

More preferably, the light emitting material of the present invention comprises the complex of formula (IIA):

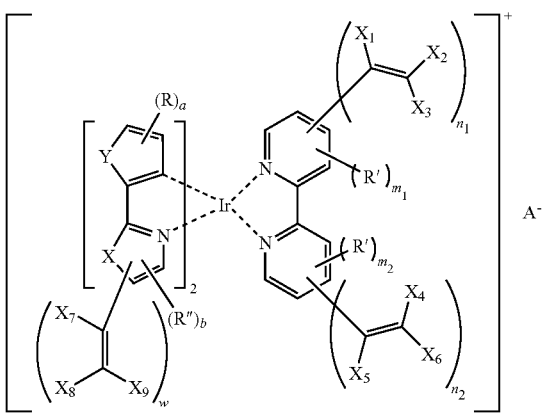

(IIA)

wherein:

$X_1, X_2, X_3, X_4, X_5, X_6$, X, Y, R, R', $n_1, n_2, m_1, m_2$, a and $A^-$ have the same meanings as defined above;

$X_7, X_8$ and $X_9$ are the same or different at each occurrence and are independently selected from hydrogen, alkyl, aryl, heteroaryl and alkyl, each of which may be substituted by at least one substituent;

R" is the same or different at each occurrence and represents —F, —Cl, —Br, —$NO_2$, —ON, a straight or branched $C_{1-20}$ alkyl, a $C_{3-20}$ cyclic alkyl, a straight or branched $C_{1-20}$ alkoxy, a $C_{1-20}$ dialkylamino, a $C_{4-14}$ aryl or a $C_{4-14}$ heteroaryl that may be substituted by one or more non aromatic radicals, wherein a plurality of substituents R" (either on the same ring or on two different rings) may collectively form an additional mono- or polycyclic ring system (optionally aromatic);

b is an integer from 0 to 3; and w is an integer from 1 and 4.

Among the complexes of the present invention, the preferred ones are those wherein $X_1, X_2, X_3, X_4, X_5$, and $X_6$ are each independently selected from hydrogen and unsubstituted or substituted aryl groups.

More preferred ones are those wherein: two of $X_1, X_2$, and $X_3$ are hydrogen while the remaining one is a benzoic acid radial; two of $X_4, X_5$, and $X_6$ are hydrogen while the remaining one is a benzoic acid radical; or two of $X_7, X_8$ and $X_9$ are hydrogen while the remaining one is a benzoic acid radical.

The complex of formula (III), which is shown below, produced excellent results:

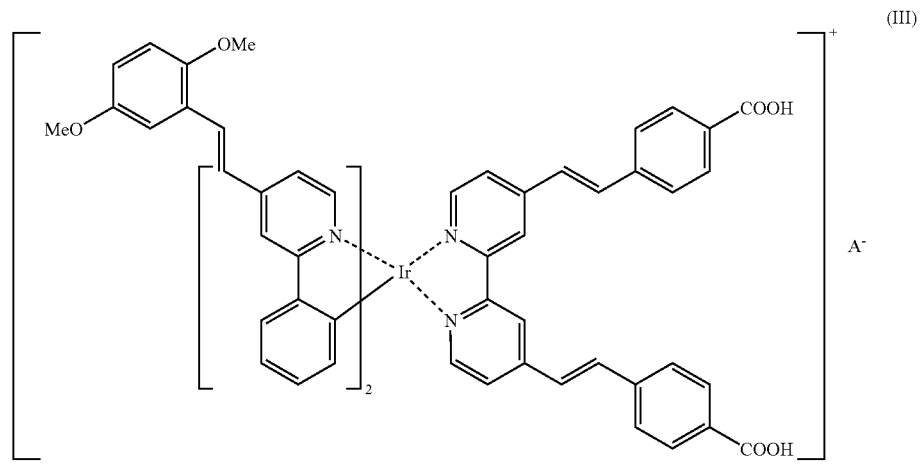

wherein A⁻ has the same meaning as above defined.

The complex of formula (III), which comprises 2-phenyl-N-pyridine (ppy) orthometalated ligands and a bidentate bipyridine (bpy) bearing conjugated ethylenically unsaturated substituents as ancillary ligand, is particularly advantageous for the present invention due to its emission in the red region with high colour purity.

The synthesis of complex of formula (I) (i.e., metal complex comprising two orthometalated ligands (C^N ligands) and a neutral bidentate bipyridine ligand (N^N)) can be accomplished by any known method. The details of synthetic methods, which are suitable for preparing the complexes of formula (I), are amply disclosed in the following literatures: "Inorg. Chem.," No. 30, pg. 1685 (1991); "Inorg. Chem.," No. 27, pg. 3464 (1988); "Inorg. Chem.," No. 33, pg. 545 (1994); "Inorg. Chem. Acta," No. 181, pg. 245 (1991); "J. Orgonomet. Chem.," No. 35, pg. 293 (1987); and "J. Am. Chem. Soc.," No. 107, pg. 1431 (1985).

Generally, according to the first embodiment of the present invention, the complexes that comply with formula (I) can be prepared according to the following reaction scheme:

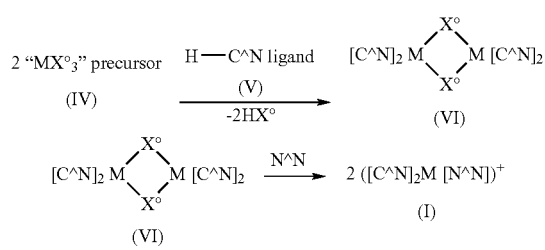

Acid forms of the orthometalated ligands (H—C^N) and ancillary ligands (N^N) are commercially available or can be easily synthesized by using well-known organic synthesis reaction pathways.

In particular, orthometalated ligands (H—C^N) can be prepared with good to excellent yields by Suzuki coupling the substituted pyridine compound with corresponding arylboronic acids, as described in Olivier Lohse, et al (The Palladium Catalyzed Suzuki Coupling of 2- and 4-chloropyridines. *Syn. Lett.* 1999, No. 1, pgs. 15-18) and U.S. Pat. No. 6,670,645 (DU PONT DE NEMOURS) 30 Dec. 2003.

Synthetic methods, which are particularly adapted for preparing the fluorinated orthometalated ligands (H—C^N), are described in JP 2003113164 A (MITSUBISHI MATERIALS CORP) 18 Apr. 2003 and JP 2003113163 A (MITSUBISHI MATERIALS CORP) 18 Apr. 2003.

If the transition metal is iridium, then trihalogenated iridium (III) compounds such as $IrCl_3 \cdot H_2O$, hexahalogenated Iridium (III) compounds such as $M°_3 IrX°_6$ (wherein X° is a halogen (preferably Cl) and M° is an alkaline metal (preferably K)) and hexahalogenated iridium (IV) compounds such as $M°_2 IrX°_6$ (wherein X° is a halogen (preferably Cl) and M° is an alkaline metal (preferably K)) ("Ir halogenated precursors") can be used as starting materials to synthesize the complexes of formula (I).

$[C^\wedge N]_2 Ir(\mu\text{-}X°)_2 Ir[C^\wedge N]_2$ complexes (compound VI, wherein M=Ir), wherein X° is a halogen (preferably Cl), can be prepared from said Ir halogenated precursors and the appropriate orthometalated ligand by using procedures already disclosed in literatures (S. Sprouse, K. A. King, P. J. Spellane, R. J. Watts, J. Am. Chem. Soc., 1984, 106, 6647-6653; M. E. Thompson et al., Inorg. Chem., 2001, 40(7), 1704; M. E. Thompson et al., J. Am. Chem. Soc., 2001, 123(18), 4304-4312).

Preferably, reaction is carried out by using an excess of the neutral form of the orthometalated ligand (H—C^N). Further, high-boiling temperature solvents are preferred.

The term "high-boiling temperature solvent" is intended to denote a solvent having a boiling point of at least 80° C., preferably at least 85° C., and more preferably at least 90° C. For instance, suitable solvents are methoxyethanol, ethoxyethanol, glycerol, dimethylformamide (DMF), N-methylpyrrolidone (NMP), dimethylsulfoxide (DMSO) and the like, wherein said solvents can be used as is or in admixture with water.

Optionally, reaction can be carried out in the presence of a suitable Brønsted base such as metal carbonates (especially potassium carbonate ($K_2CO_3$)), metal hydrides (especially sodium hydride (NaH)), metal ethoxide or metal methoxide (especially $NaOCH_3$ and $NaOC_2H_5$), alkylammonium hydroxides (especially tetramethylammonium hydroxide) or imidazolium hydroxides.

A nucleophilic substitution at the metal atom with a suitable ligand (N^N), which is to form corresponding ($[C^\wedge N]_2 Ir[N^\wedge N])^+ A^-$ (formula I, wherein Me=Ir), is preferably carried out by roughly contacting a stoichiometric amount of ligand N^N with bridged intermediate (VI) in a suitable solvent.

Polar aprotic solvents are generally preferred for this reaction. A solvent, which produced particularly good results, is methylene dichloride ($CH_2Cl_2$).

The present invention is also directed to the use of a light emitting material in the emissive layer of an organic light emitting device (OLED).

Furthermore, the present invention is directed to the use of a light emitting material as dopant in a host layer, thus functioning as an emissive layer in an organic light emitting device.

If the light emitting material is used as dopant in a host layer, it is generally used in an amount of at least 1% wt, preferably at least 3% wt, and more preferably at least 5% wt with respect to the total weight of the host and the dopant. Further, it is generally used in an amount of at most 25% wt, preferably at most 20% wt, and more preferably at most 15% wt.

The present invention is also directed to an organic light emitting device (OLED) comprising an emissive layer (EML), wherein said emissive layer comprises the light emitting material described above. The OLED can optionally comprise a host material (wherein the light emitting material is preferably present as a dopant), wherein said host material is adapted to luminesce when a voltage is applied across the device structure.

The OLED generally comprises:
a glass substrate;
a generally transparent anode such as an indium-tin oxide (ITO) anode;
a hole transporting layer (HTL);
an emissive layer (EML);
an electron transporting layer (ETL);
a generally metallic cathode such as an Al layer.

For a hole conducting emissive layer, one may have an exciton blocking layer, notably a hole blocking layer (HBL) between the emissive layer and the electron transporting layer. For an electron conducting emissive layer, one may have an exciton blocking layer, notably an electron blocking layer (EBL) between the emissive layer and the hole transporting layer. The emissive layer may be equal to the hole transporting layer (in which case the exciton blocking layer is near or at the anode) or the electron transporting layer (in which case the exciton blocking layer is near or at the cathode).

The emissive layer may be formed with a host material, wherein the light emitting material resides as a guest. Alternatively, the emissive layer may essentially comprise the light emitting material itself. In the former case, the host material may be a hole-transporting material selected from the group consisting of substituted tri-aryl amines. Preferably, the emissive layer is formed with a host material, wherein the light emitting material resides as a guest. The host material may be an electron-transporting material selected from the group consisting of metal quinoxolates (e.g., aluminum quinolate ($Alq_3$), lithium quinolate (Liq), oxadiazoles and triazoles. An example of the host material is 4,4'-N,N'-dicarbazole-biphenyl ["CBP"], which can be characterized by the following formula:

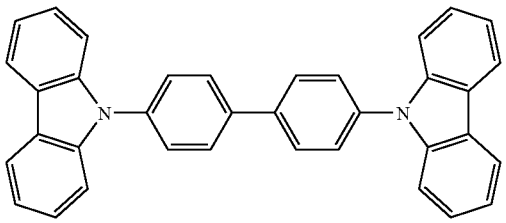 [SMILES: c1ccc2c(c1)c1ccccc1n2-c1ccc(-c2ccc(-n3c4ccccc4c4ccccc43)cc2)cc1]

CBP

Optionally, the emissive layer may also contain a polarization molecule, which is present as a dopant in said host material and having a dipole moment, that generally affects the wavelength of light emitted when said light emitting material used as a dopant luminesces.

A layer formed from an electron transporting material is used to transport electrons into the emissive layer comprising the light emitting material and the optional host material. The electron transporting material may be an electron-transporting matrix selected from the group consisting of metal quinoxolates (e.g., $Alq_3$ and Liq), oxadiazoles and triazoles. An example of an electron transporting material is tris-(8-hydroxyquinoline)aluminum of formula ["$Alq_3$"]:

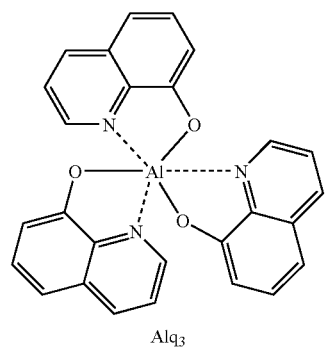

$Alq_3$

A layer formed from a hole transporting material is used to transport holes into the emissive layer comprising the light emitting material and the optional host material. An example of a hole transporting material is 4,4'-bis[N-(1-naphthyl)-N-phenylamino]biphenyl ["α-NPD"].

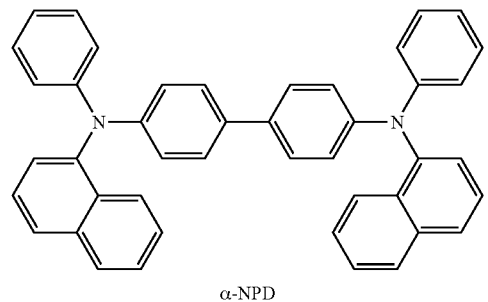 [SMILES: c1ccc(N(c2ccc(-c3ccc(N(c4ccccc4)c4cccc5ccccc45)cc3)cc2)c2cccc3ccccc23)cc1]

α-NPD

The use of an exciton blocking layer ("barrier layer") to confine excitons within the luminescent layer ("luminescent zone") is greatly preferred. For a hole-transporting host, the blocking layer may be placed between the emissive layer and the electron transport layer. An example of a material for such a barrier layer is 2,9-dimethyl-4,7-diphenyl-1,10-phenanthroline (also referred to as bathocuproine or "BCP"), which has the following formula:

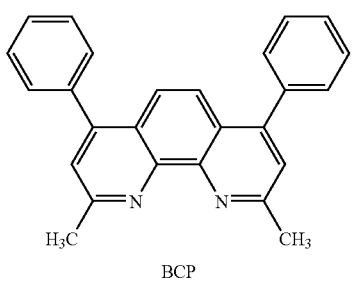
BCP

The OLED preferably has a multilayer structure (as depicted in FIG. 1), wherein: 1 is a glass substrate; 2 is an ITO layer; 3 is a HTL layer comprising α-NPD; 4 is an EML comprising CBP as host material and the light emitting material as dopant in an amount of about 8% wt with respect to the total weight of host plus dopant; 5 is a HBL comprising BCP; 6 is an ETL comprising Alq$_3$; and 7 is an Al layer cathode.

EXAMPLES

Synthesis of 2-phenyl-4-(2,5-dimethoxystyryl)pyridine

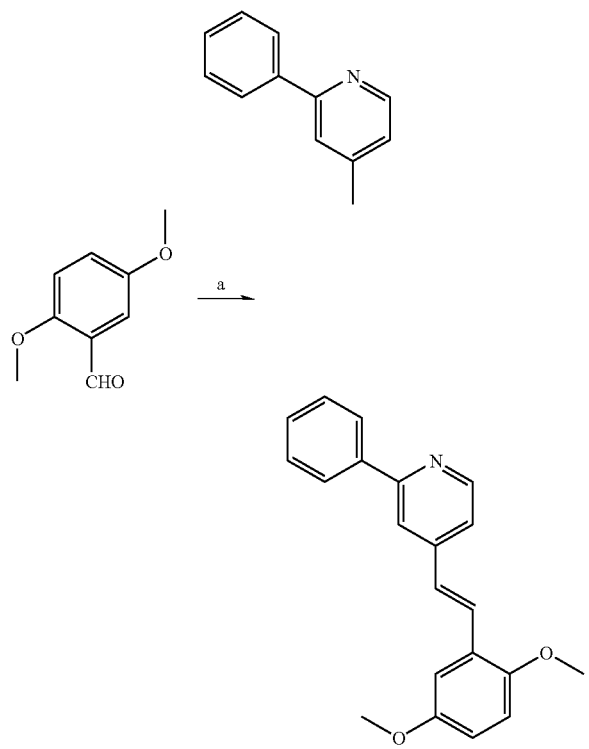

a) tBuOK, DMF, rt

To a mixture of 2-phenyl-4-methylpyridine hydrochloride (1 g, 4.9 mmol) and 2,5-dimethoxybenzaldehyde (1.2 g, 7.3 mmol) in anhydrous DMF (40 ml), solid t-BuOK (2 g, 18 mmol) was added. The resulting mixture was stirred overnight at 80° C. under nitrogen. After evaporating DMF, Et$_2$O was added thereto and the precipitate was filtered and washed with water. The solid was purified by column chromatography (SiO$_2$, CH$_2$Cl$_2$/MeOH, 99/1) to afford 0.6 g (39%) of the desired compound as a yellow solid.

Synthesis of [(2-phenyl-4-(2,5-dimethoxystyryl)pyridine)$_2$IrCl]$_2$

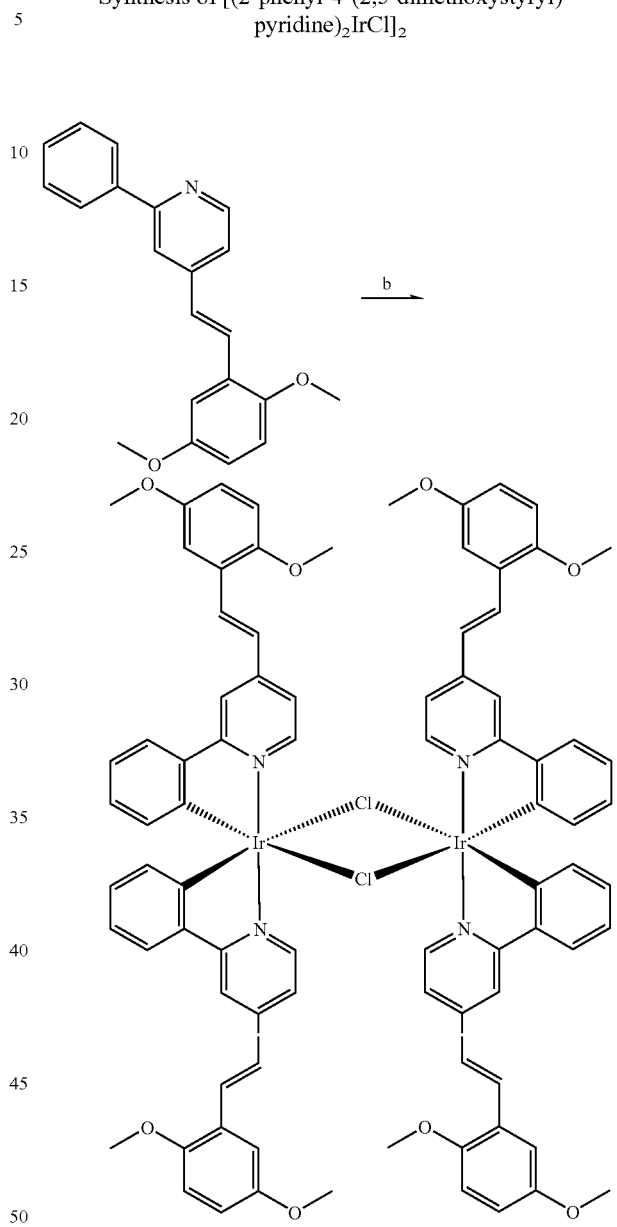

b) IrCl$_3$.H$_2$O, EtOCH$_2$CH$_2$OH/H$_2$O, Δ.

1 equivalent of IrCl$_3$.3H$_2$O and 2.5 equivalents of 2-phenyl-4-(2,5-dimethoxystyryl)pyridine were heated at 110° C. in a mixture of 2-ethoxyethanol and water (3/1, v/v) overnight under nitrogen. After being cooled to room temperature, the resulting precipitate was filtered off, successively washed with methanol (than Et$_2$O) and finally dried to afford the desired dimer. Because of the low solubility of this compound, its $^1$H-NMR was recorded in DMSO-d$^6$ as its [C^N]$_2$Ir(Cl)(DMSO) derivative.

$^1$H-NMR (DMSO-d$^6$, 298K, 200 MHz, δ ppm) 3.80 (s, 12H), 3.88 (s, 12H), 5.85 (d, J=7 Hz, 1H), 6.31 (d, J=7 Hz, 1H), 6.70-7.90 (m, 42H), 8.26 (s, 1H), 8.32 (s, 1H), 9.45 (d, J=7 Hz, 1H), 9.75 (d, J=7 Hz, 1H).

Synthesis of [(2-phenyl-4-(2,5-dimethoxystyryl)pyridine)$_2$Ir(4,4'-dicarboxylic acid 2,2'-bipyridine] [Comparative Complex (VII)]

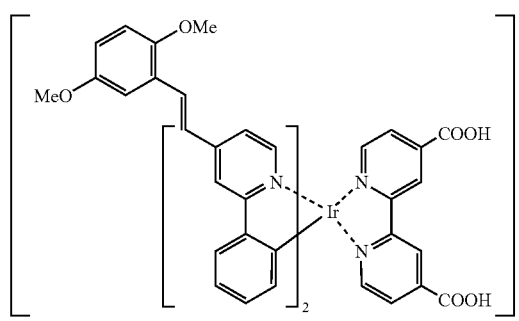

(VII)

[(2-phenyl-4-(2,5-dimethoxystyryl)pyridine)$_2$IrCl]$_2$ (122 mg, 0.071 mmol), 4,4'-dicarboxylic acid 2,2'-bipyridine (40 mg, 0.164 mmol) and tetrabutylammoniumhydroxide 30 hydrate (261 mg, 0.326 mmol) were refluxed in CH$_2$Cl$_2$ (100 ml) for 6 hours under argon. The resulting orange solution was concentrated to 5 mL and was crystallized by slow diffusion of ethanol. The light yellow precipitate was filtered, washed with Et$_2$O and air dried to afford 50 mg of the desired complex (yield: 33%).

Synthesis of [(2-phenyl-4-(2,5-dimethoxystyryl)pyridine)$_2$Ir(4,4'-dicarboxylic acid styryl)-2,2'-bipyridine] [Complex (III)]

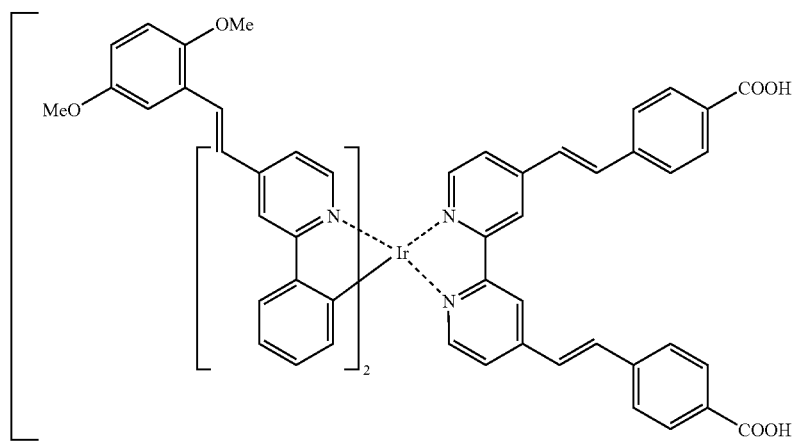

(III)

[(2-phenyl-4-(2,5-dimethoxystyryl)pyridine)$_2$IrCl]$_2$ (83 mg, 0.048 mmol), (4,4'-paradicarboxylic acid styryl)-2,2'-bipyridine (44 mg, 0.095 mmol) and tetrabutylammoniumhydroxide 30 hydrate (194 mg, 0.242 mmol) were refluxed in DMF (30 ml) for 8 hours under argon. The resulting solution was evaporated to dryness and the resulting solid was recrystallized from methanol to afford 100 mg of the desired complex (yield: 80%).

The emission spectrum of complex (III) shows its maxima at around 710 nm (corresponding to red emission), with an emission intensity largely exceeding that of reference complex (VII) and a red-shift of roughly 20 nm with respect to reference complex (VII), thus enabling pure red color emission to be obtained.

The invention claimed is:
1. A complex of formula (I):

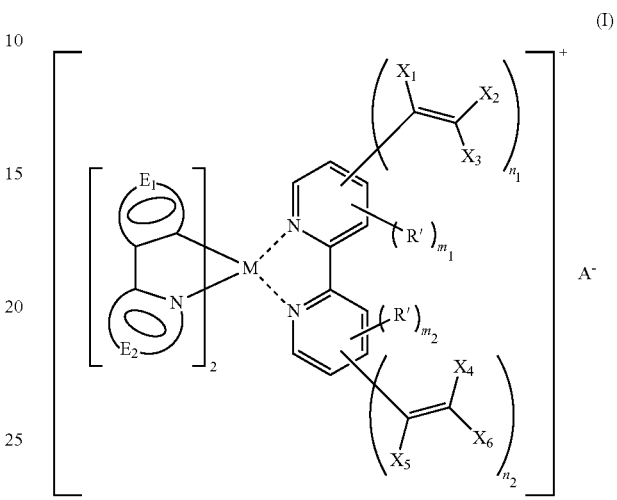

(I)

wherein:
M represents a transition metal having an atomic number of at least 40;
E$_1$ represents an aromatic or heteroaromatic ring optionally condensed with additional aromatic moieties or non aromatic cycles, wherein said ring optionally has one or more substituents and optionally forms a condensed structure with the ring comprising E$_2$, and wherein said ring coordinates to metal M by using a Sp$^2$ hybridized carbon;
E$_2$ represents a N-containing aromatic ring optionally condensed with additional aromatic moieties or non aromatic cycles, wherein said ring optionally has one or more substituents and optionally forms a condensed structure with the ring comprising E$_1$, and wherein said ring coordinates to metal M by using a Sp$^2$ hybridized nitrogen;

R' is the same or different at each occurrence and is selected from the group consisting of —H, —F, —Cl, —Br, —NO$_2$, —CN, a straight or branched C$_{1-20}$ alkyl, a C$_{3-20}$ cyclic alkyl, a straight or branched C$_{1-20}$ alkoxy, a C$_{1-20}$ dialkylamino, a C$_{4-14}$ aryl, and a C$_{4-14}$ heteroaryl that is optionally substituted by one or more non aromatic radicals, wherein optionally a plurality of substituents R', either on the same ring or on two different rings, collectively form an additional mono- or polycyclic ring system, optionally aromatic;

X$_1$, X$_2$, X$_3$, X$_4$, X$_5$ and X$_6$ are the same or different at each occurrence and are independently selected from the group consisting of hydrogen, alkyl, aryl, heteroaryl and alkyl, each of which is optionally substituted by at least one substituent;

A$^-$ is a counter anion; and n$_1$, n$_2$, m$_1$ and m$_2$ are the same or different at each occurrence and represent an integer from 0 to 4, wherein n$_1$+m$_1$=4 and n$_2$+m$_2$=4, provided that n$_1$ and n$_2$ are not zero at the same time.

2. The complex of claim 1, represented by formula (II):

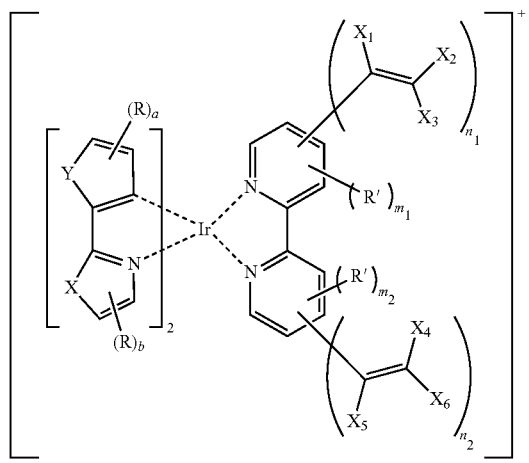

(II)

wherein:

X$_1$, X$_2$, X$_3$, X$_4$, X$_5$, X$_6$, R', n$_1$, n$_2$, m$_1$, m$_2$ and A$^-$ have the same meanings as defined in claim 1;

X is selected from the group consisting of —CH=CH—, —CR=CH—, —CR=CR—, N—H, N—R$^1$, O, S, and Se;

Y is selected from the group consisting of —CH=CH—, —CR=CH—, —CR=CR—, N—H, N—R$^1$, O, S, and Se;

R is the same or different at each occurrence and represents —F, —Cl, —Br, —NO$_2$, —CN, a straight or branched C$_{1-20}$ alkyl, a C$_{3-20}$ cyclic alkyl, a straight or branched C$_{1-20}$ alkoxy, a C$_{1-20}$ dialkylamino, a vinyl that is optionally substituted by one or more aromatic or non aromatic radicals, a C$_{4-14}$ aryl, or a C$_{4-14}$ heteroaryl that is optionally substituted by one or more non aromatic radicals, wherein optionally a plurality of substituents R, either on the same ring or on two different rings, collectively form an additional mono- or polycyclic ring system optionally aromatic;

a is an integer from 0 to 4; and b is an integer from 0 to 4.

3. The complex of claim 2, represented by formula (IIA):

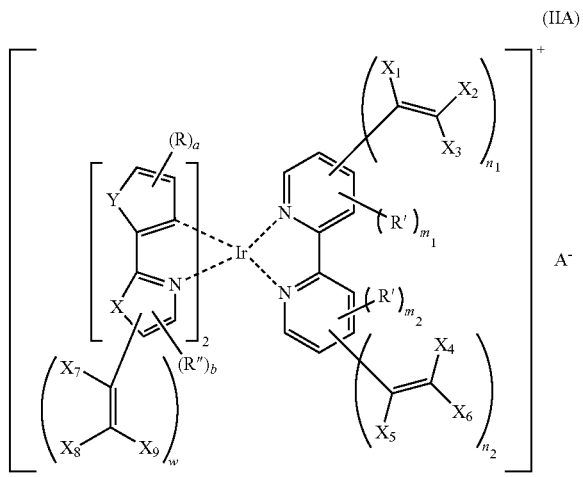

(IIA)

wherein:

X$_1$, X$_2$, X$_3$, X$_4$, X$_5$, X$_6$, X, Y, R, R', n$_1$, n$_2$, m$_1$, m$_2$, a and A$^-$ have the same meanings as defined in claim 2;

X$_7$, X$_8$ and X$_9$ are the same or different at each occurrence and are independently selected from the group consisting of hydrogen, alkyl, aryl, heteroaryl and alkyl, each of which is optionally substituted by at least one substituent;

R" is the same or different at each occurrence and represents —F, —Cl, —Br, —NO$_2$, —CN, a straight or branched C$_{1-20}$ alkyl, a C$_{3-20}$ cyclic alkyl, a straight or branched C$_{1-20}$ alkoxy, a C$_{1-20}$ dialkylamino, a C$_{4-14}$ aryl or a C$_{4-14}$ heteroaryl that is optionally substituted by one or more non aromatic radicals, wherein optionally a plurality of substituents R", either on the same ring or on two different rings, collectively form an additional mono- or polycyclic ring system optionally aromatic;

b is an integer from 0 to 3; and w is an integer from 1 and 4.

4. The complex according to claim 1, wherein X$_1$, X$_2$, X$_3$, X$_4$, X$_5$, and X$_6$ are each independently selected from the group consisting of hydrogen, unsubstituted aryl groups and substituted aryl groups.

5. The complex according to claim 4, wherein two of X$_1$, X$_2$, and X$_3$ are hydrogen and the remainder is a benzoic acid radical.

6. The complex according to claim 4, wherein two of X$_4$, X$_5$, and X$_6$ are hydrogen and the remainder is a benzoic acid radical.

7. The complex according to claim 3, wherein two of X$_7$, X$_8$ and X$_9$ are hydrogen and the remainder is a benzoic acid radical.

8. The complex according to claim 7, represented by formula (III):

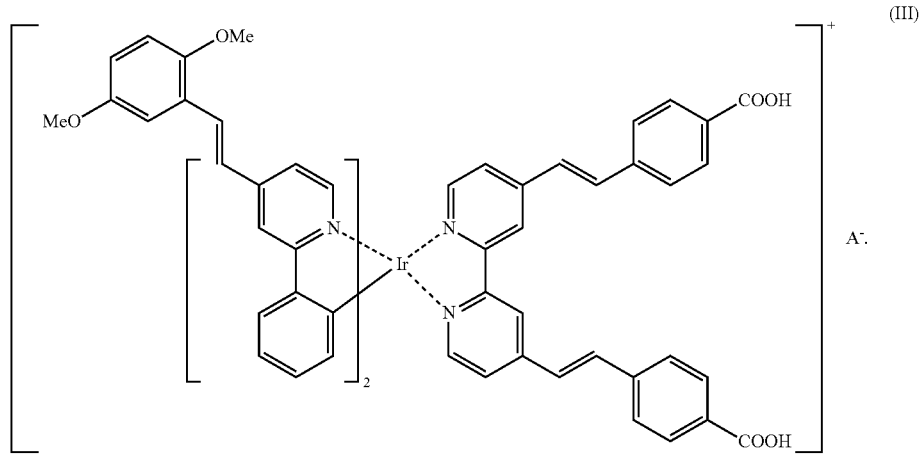

(III)

9. A light emitting material comprising the complex according to claim 1.

10. A method for forming an emissive layer of an organic light emitting device, comprising using the light emitting material according to claim 9 in the emissive layer.

11. A method for forming an emissive layer of an organic light emitting device, comprising using the light emitting material according to claim 9 as dopant in a host layer, thereby functioning as the emissive layer in the organic light emitting device.

12. An organic light emitting device (OLED) comprising an emissive layer (EML), wherein said emissive layer comprises the light emitting material according to claim 9, and optionally a host material.

13. A display device comprising the organic light emitting device according to claim 12.

* * * * *